United States Patent [19]
Houston et al.

[11] Patent Number: 5,613,970
[45] Date of Patent: Mar. 25, 1997

[54] ORTHOPAEDIC INSTRUMENTATION ASSEMBLY HAVING AN OFFSET BUSHING

[75] Inventors: Michelle L. Houston, Warsaw; Steven A. Zawadzki, Pierceton; Kevin M. Greig, Leesburg; Jerry L. Aikins, Warsaw, all of Ind.

[73] Assignee: Zimmer, Inc., Warsaw, Ind.

[21] Appl. No.: 498,730

[22] Filed: Jul. 6, 1995

[51] Int. Cl.⁶ ..................................................... A61B 17/56
[52] U.S. Cl. .................................. 606/88; 606/86; 606/87
[58] Field of Search ..................... 606/96, 62, 79, 606/80, 86, 87, 88, 89; 623/20

[56] References Cited

U.S. PATENT DOCUMENTS

| | | | |
|---|---|---|---|
| D. 274,094 | 5/1984 | Kenna . | |
| 4,357,716 | 11/1982 | Brown . | |
| 4,524,766 | 6/1985 | Petersen . | |
| 4,736,737 | 4/1988 | Fargie et al. . | |
| 4,787,383 | 11/1988 | Kenna . | |
| 4,791,919 | 12/1988 | Elloy et al. . | |
| 4,822,362 | 4/1989 | Walker et al. | 623/20 |
| 4,822,365 | 4/1989 | Walker et al. | 623/20 |
| 4,936,853 | 6/1990 | Fabian et al. | 623/20 |
| 4,985,037 | 1/1991 | Petersen | 623/20 |
| 5,002,547 | 3/1991 | Poggie et al. | 606/88 |
| 5,002,581 | 3/1991 | Paxson et al. | 623/23 |
| 5,047,061 | 9/1991 | Brown | 623/23 |
| 5,053,037 | 10/1991 | Lackey | 606/79 |
| 5,062,852 | 11/1991 | Dorr et al. | 623/20 |
| 5,100,408 | 3/1992 | Lackey | 606/79 |
| 5,108,396 | 4/1992 | Lackey et al. | 606/62 |
| 5,112,336 | 5/1992 | Krevolin et al. | 606/96 |
| 5,116,338 | 5/1992 | Poggie et al. | 606/90 |
| 5,133,760 | 7/1992 | Petersen et al. | 623/20 |
| 5,135,529 | 8/1992 | Paxson et al. | 606/85 |
| 5,141,513 | 8/1992 | Fortune et al. | 606/96 |
| 5,201,882 | 4/1993 | Paxson | 623/23 |
| 5,250,050 | 10/1993 | Poggie et al. | 606/79 |
| 5,271,737 | 12/1993 | Baldwin et al. | 623/20 |
| 5,275,603 | 1/1994 | Ferrante et al. | 606/86 |
| 5,282,803 | 2/1994 | Lackey | 606/80 |
| 5,282,866 | 2/1994 | Cohen et al. | 623/20 |
| 5,290,313 | 3/1994 | Heldreth | 623/20 |
| 5,342,367 | 8/1994 | Ferrante et al. | 606/86 |
| 5,356,414 | 10/1994 | Cohen et al. | 606/88 |
| 5,411,505 | 5/1995 | Mumme | 606/88 |
| 5,417,695 | 5/1995 | Axelson, Jr. | 606/89 |

FOREIGN PATENT DOCUMENTS

WO94/05211   3/1994   WIPO .

OTHER PUBLICATIONS

Honmedica—Duraconcept—Design Concepts of the Duracon Total Knee System—c1993.
Johnson & Johnson Orthopaedics—P.F.C. Modular Knee System w/Specialist Instruments—No date available.
Smith & Nephew Richards Inc.—Genesis Total Knee System—No date available.
Zimmer—Porous MG II Total Knee—Cross-Stemmed Tibial Tray—lit. #97–8510–05–c1992.
Zimmer, Inc.—State-of-the-Art Revision Instrumentation–1994.

Primary Examiner—Michael Buiz
Assistant Examiner—David O. Reip
Attorney, Agent, or Firm—Margaret L. Geringer

[57] ABSTRACT

The invention is directed to an orthopaedic instrumentation assembly 10 located relative to an intramedullary member 12, wherein the intramedullary member is disposed at least partially within a bone. The instrumentation assembly 10 includes an offset bushing 16 having a longitudinal axis and a bore therethrough for receiving the intramedullary member. The bore is disposed non-coaxially relative to the longitudinal axis. A sizing plate 14 has an opening 22 therein, and further includes a portion associated with the opening for receiving the bushing, wherein the bushing is rotatably supported. Upon movement of the bushing 16 or sizing plate 14, the bushing and sizing plate coact to position the sizing plate relative to each of the intramedullary member and the bone.

21 Claims, 2 Drawing Sheets

ORTHOPAEDIC INSTRUMENTATION ASSEMBLY HAVING AN OFFSET BUSHING

BACKGROUND OF THE INVENTION

1. Field of the Invention

The present invention relates to orthopaedic instrumentation, and, more particularly, relates to orthopaedic instrumentation which may be used in conjunction with a prosthesis having an offset prosthetic stem extension.

2. Description of the Related Art

It is known to provide a tibial prosthetic implant having a stem extension which is essentially centrally located relative to a base portion. However, a stem which is centrally located on the base portion may interfere with the tibial cortex as the surgeon attempts to center the tibial plate on the proximal cut tibia. Further, the intramedullary (IM) canal of the tibia may not be centrally located relative to the peripheral edges of the proximal tibia. A tibial prosthetic implant having a stem extension which is centrally located relative to a base portion may therefore not allow a proper positioning of the base portion relative to the proximal end of the tibia.

It is also known to provide a tibial prosthesis having a stem extension which is offset relative to a base portion. For example, U.S. Pat. No. 5,290,313 (Heldreth), which is assigned to the assignee of the present invention and incorporated herein by reference, discloses a tibial prosthesis having a stem extension defining a longitudinal axis thereof. The stem extension also includes a stem mounting portion which is disposed offset from the longitudinal axis, such that the longitudinal axis of the stem extension is disposed offset from the location at which the stem extension attaches to the base portion. Utilizing such a tibial prosthesis, the attachment point of the base portion is offset from the IM canal of the tibia. It is therefore possible to more accurately position the base portion of the tibial prosthesis relative to the proximal end of the tibia.

What is needed in the art is an instrumentation assembly which relatively easily prepares the proximal end of the tibia for proper positioning of a tibial prosthesis including a base portion and an offset stem extension.

SUMMARY OF THE INVENTION

The present invention is directed to an orthopaedic instrumentation assembly including a plate member which is positioned relative to an elongated member, such as an IM reamer, using an offset bushing which cooperates with the plate member and has a bore therein for receiving the elongated member.

The invention comprises, in one form thereof, an orthopaedic instrumentation assembly located relative to an intramedullary member, wherein the intramedullary member is disposed at least partially within a bone. The instrumentation assembly includes a bushing having a longitudinal axis and a bore therethrough for receiving the intramedullary member. The bore is disposed noncoaxially relative to the longitudinal axis. A sizing plate has an opening therein, and further includes a portion associated with the opening for receiving the bushing, wherein the bushing is rotatably supported. Upon movement of the bushing or sizing plate, the bushing and sizing plate coact to position the sizing plate relative to each of the intramedullary member and the bone.

An advantage of the present invention is that the plate member can be supportably moved to a desired position relative to the elongated member, and thereat affixed to the bone.

Another advantage is that the invention allows the use of a prosthesis having an offset stem, while at the same time optimizing the coverage of the prosthesis on the bone.

Yet another advantage is that when the plate member is in an assembled position, the plate member can be moved relative to the elongated member by moving either the plate member or the offset bushing.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
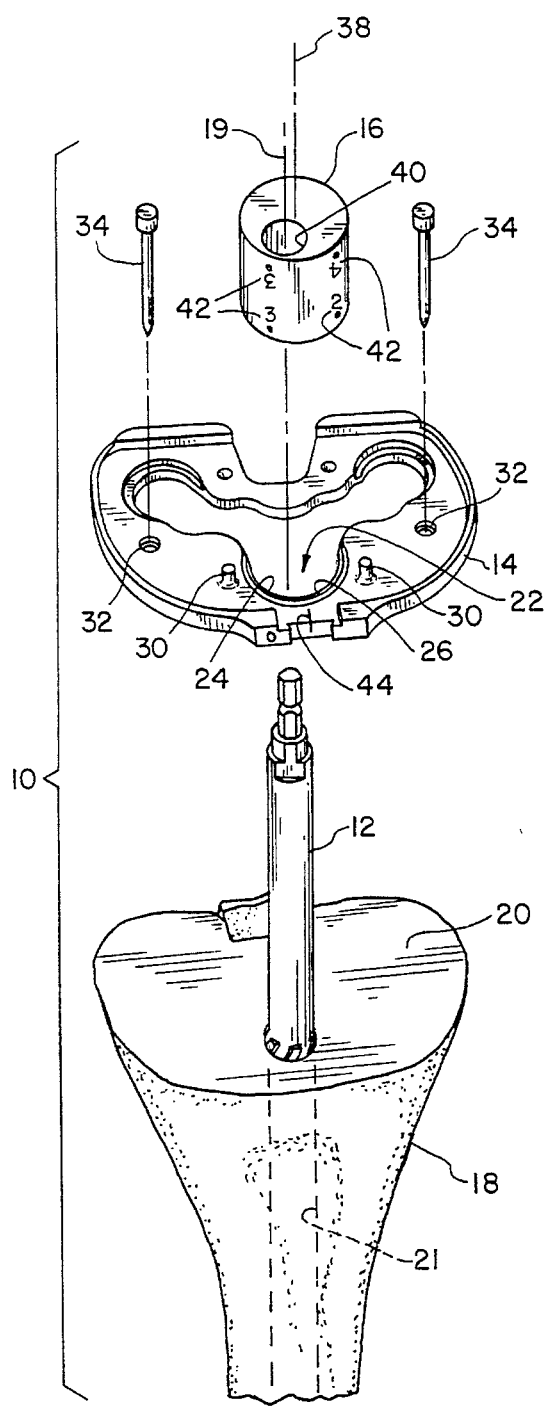
FIG. 1 is an exploded, perspective view of an embodiment of the instrumentation assembly of the present invention.
Figure 2:
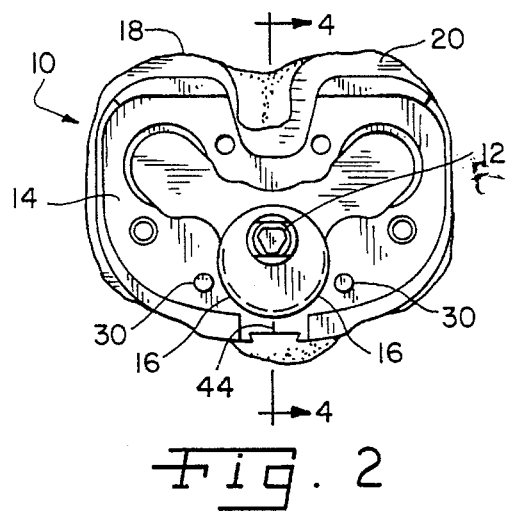
FIG. 2 is a top view of the instrumentation assembly shown in FIG. 1 when in an assembled position, with the offset bushing and tibial sizing plate in respective first positions.
Figure 4:
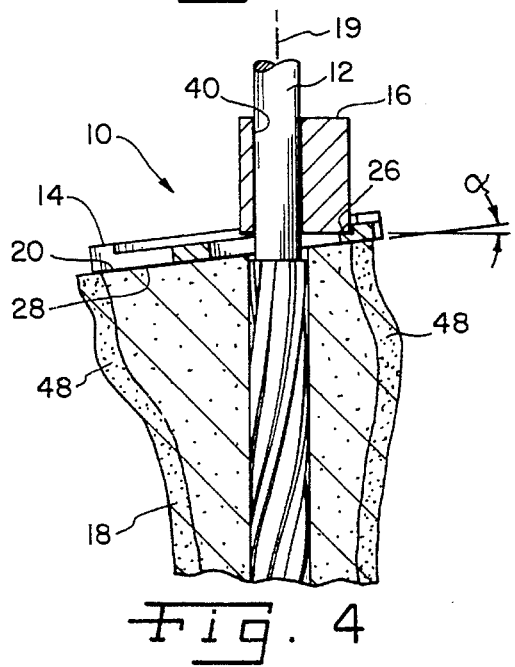
FIG. 4 is a side, sectional view taken along line 4—4 in FIG. 2.

Referring now to the drawings, and particularly to FIGS. 1, 2 and 4, an orthopaedic instrumentation assembly 10 of the present invention includes an elongated member 12, plate member 14 and offset bushing 16.

Elongated member 12 is attached to a bone 18. In the embodiment shown, bone 18 is a tibia, and elongated member 12 is an IM member disposed within an IM canal of tibia 18. More particularly, IM member 12 is an IM reamer disposed within IM canal 21 of tibia 18. IM reamer 12 defines an axis of alignment or an axis of rotation 19. Tibia 18 includes a proximal end 20 which has been previously shaped using appropriate instrumentation, such as cutting instrumentation.

Plate member 14 is constructed as a tibial sizing plate in the embodiment shown, and includes an opening 22 therein defining an inner periphery 24 thereof. A recessed shoulder 26 (FIGS. 1 and 4) is disposed within opening 22 and about inner periphery 24. Tibial sizing plate 14 also includes a bottom surface 28 which is adapted for placement against proximal end 20 of tibia 18. As shown in FIG. 4, recessed shoulder 26 is disposed at an acute angle relative to bottom surface 28. More particularly, recessed shoulder 26 is disposed at an acute angle α (FIG. 4) between about 0° to 10° relative to bottom surface 28, and more preferably disposed at an acute angle α of approximately 7° relative to bottom surface 28.

Tibial sizing plate 14 further includes locating pins 30 adapted for engagement with a drill guide (to be discussed hereinafter), and holes 32 for receiving respective fixation pins 34 (FIG. 1). In the embodiment shown in FIGS. 1–4, tibial sizing plate 14 has an outer periphery which is generally symmetrical in shape about an axis of symmetry 36, and opening 22 is disposed along axis of symmetry 36.

Offset bushing 16 is sized and configured for placement within opening 22 and against recessed shoulder 26 (FIGS. 1, 2 and 4). Bushing 16 defines a central longitudinal axis 38, and has a bore 40 extending therethrough for receiving IM reamer 12. In an assembled position, bore 40 is disposed coaxially relative to axis of rotation 19, and offset from, i.e., non-coaxial relative to, longitudinal axis 38. Bore 40 extends generally parallel to longitudinal axis 38 in the embodiment shown, but can be disposed non-parallel to longitudinal axis 38. In particular, bore 40 has an axis of rotation which is disposed offset from and parallel to longitudinal axis 38 a distance of between about 0.1 to 12 millimeters, and preferably is disposed offset from and parallel to longitudinal axis 38 a distance of approximately 4.5 millimeters. A plurality of offset bushings 16 may be provided to offer different offset distances. Disposed about the circumferential periphery of bushing 16 are a plurality of alignment indicia 42 which may be aligned relative to an alignment mark 44 on tibial sizing plate 14. Alignment indicia 42 provide a cross-reference between the positioning of tibial sizing plate 14 and a provisional and/or implant tibial prosthesis having an offset stem extension (not shown). That is, alignment indicia 42 are disposed about the periphery of bushing 16 at predetermined locations, and corresponding alignment indicia are disposed on the offset stem extension of the tibial prosthesis provisional and/or implant. It is thus possible to generally align the offset stem extension of the tibial prosthesis provisional and/or implant dependent on the location of alignment indicia 42 relative to alignment mark 44 after positioning tibial sizing plate 14.

It is to be noted that bushing 16 includes alignment indicia 42 at each longitudinal end thereof to enable either end of bushing 16 to be positioned against recessed shoulder 26 on plate 14. In the embodiment shown, alignment indicia 42 are in the form of numbered dots formed around the circumferential periphery of bushing 16 at each longitudinal end thereof. The bushing 16 is numbered at each end from 1 to 4 with the numbers spaced equal distances about the circumferential periphery of bushing 16. The sequence of the numbering associated with each indicia is adapted to provide the proper relative alignment as bushing 16 is flipped over, such that one longitudinal end or the other is disposed against recessed shoulder 26. It is understood that other patterns or types of suitable alignment indicia could be utilized.

Figure 3:
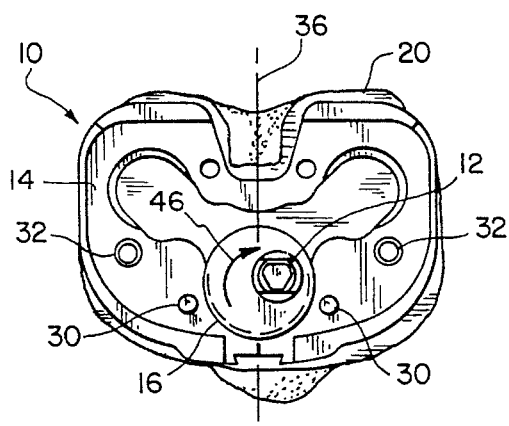
FIG. 3 is a top view of the instrumentation shown in FIG. 2, with the offset bushing and tibial sizing plate in respective second positions.

Referring now to FIGS. 2 and 3, it is apparent that the positioning of tibial sizing plate 14 relative to proximal end 20 of tibia 18 changes dependent upon the rotational orientation of bushing 16 relative to IM reamer 12. When in an assembled position, movement of bushing 16 or tibial sizing plate 14 relative to IM reamer 12 causes a resultant movement of the other of bushing 16 or tibial sizing plate 14 relative to IM reamer 12. For example, rotational movement of bushing 16 in the direction of arrow 46 causes a resultant sliding movement of tibial sizing plate 14 relative to IM reamer 12. Likewise, a force applied to tibial sizing plate 14 causing a sliding motion thereof results in a rotational movement of bushing 16 relative to IM reamer 12.

A plurality of tibial sizing plates 14 are available having different M-L and A-P dimensions corresponding to various sizes of tibial implants, as is known in the art to optimize the coverage of the tibial implant on the proximal end 20 of bone 18. Utilizing orthopaedic instrumentation assembly 10 of the present invention as described above, it is possible to further optimize the position of tibial sizing plate 14 relative to IM canal 21 such that tibial sizing plate 14 is substantially in contact at the periphery thereof with cortical bone or rim 48 of tibia 18.

Figure 5:
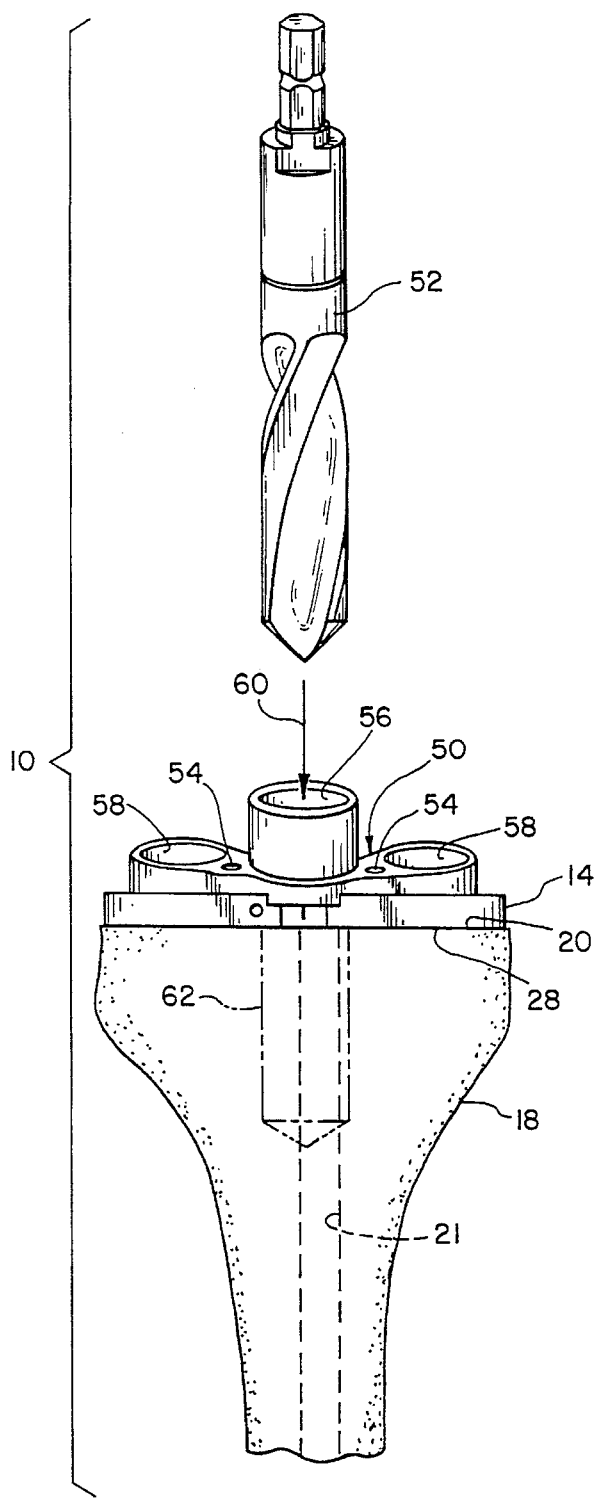
FIG. 5 is a front view of the instrumentation assembly shown in FIG. 1 with the tibial sizing plate and drill guide in an assembled position on the proximal end of a tibia, and with a stem drill shown in relation to the drill guide.

Referring now to FIG. 5, orthopaedic instrumentation assembly 10 is shown as further including a drill guide 50 and stem drill 52. Drill guide 50 includes holes 54 which are sized for receiving locating pins 30 (FIGS. 1–3) therein. Locating pins 30 and holes 54 prevent relative sliding movement between drill guide 50 and tibial sizing plate 14. Drill guide 50 further includes a stem drill guide opening 56 and tibial peg drill guide openings 58. Stem drill guide opening 56 is sized to receive stem drill 52 therein, such as indicated by directional arrow 60. Stem drill guide opening 56 guides stem drill 52 such that a recess 62 (indicated by phantom lines) can be formed within tibia 18. It is to be noted that the longitudinal axis of recess 62 is disposed offset from the longitudinal axis of IM canal 21. Recess 62 therefore allows the use of a tibial prosthesis having an offset stem extension to thereby properly position the base portion of the prosthesis relative to proximal end 20 of tibia 18. (This orthopaedic instrumentation assembly 10 of the present invention is particularly suitable for rise with the offset stem extension of U.S. Pat. No. 5,290,313, although it is not limited thereto.) Tibia peg drill guide openings 58 may also be provided to guide a peg drill (not shown) to shape proximal end 20 of tibia 18 for receipt of posterior extending pegs on a tibial prosthesis. It is noted that additional steps (not shown herein) may be performed to finish the bone for receiving the corresponding implant geometry, such as broaching for a stemmed plate having fins extending therefrom, etc.

Figure 6:
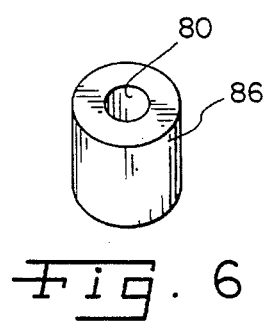
FIG. 6 is a perspective view of a symmetrical bushing.

In use, IM reamer 12 is inserted into IM canal 21 of tibia 18 in known fashion. Thereafter, tibial sizing plate 14 is positioned over reamer 12, whereby IM reamer 12 extends through opening 22. Tibial sizing plate 14 is positioned such that bottom surface 28 thereof is disposed against proximal end 20 of tibia 18. Initially, a symmetrical bushing 86 (FIG. 6) having a centrally located bore 80 is slid over IM reamer 12 to determine if the selected size tibial sizing plate 14 provides appropriate coverage of proximal end 20 of tibia 18. If so, a tibial implant having a straight or centrally located stem, rather than an offset stem may be used. If not, the symmetrical bushing is removed and the offset bushing 16 is then slid over IM reamer 12, whereby IM reamer 12 extends through bore 40 therein. Bushing 16 is then removably attached to or positioned on tibial sizing plate 14, such that bushing 16 is disposed partially within opening 22 and against recessed shoulder 26. Tibial sizing plate 14 is then moved with respect to IM reamer 12, thereby causing a rotational movement of bushing 16, as indicated, e.g., by directional arrow 46 (FIG. 3). Alternatively, bushing 16 is rotated to cause a sliding movement of sizing plate 14 relative to IM reamer 12 to locate the optimum position for plate 14. After proper positioning, tibial sizing plate 14 is attached to tibia 18 using fixation pins 34. Bushing 16 and IM reamer 12 are then removed, and drill guide 50 (FIG. 4) is attached to tibial sizing plate by aligning locating pins 30 with holes 54. Stem drill 52 is then slidingly received within stem drill guide opening 56 and used to form recess 62 in tibia 18. Once again, it is noted that additional steps may be performed to finish the bone for receiving the corresponding implant. The indicia marks on an offset stem extension may then be aligned with a base portion of a tibial prosthesis provisional and/or implant dependent upon the previous alignment of alignment indicia 42 of bushing 16 with alignment mark 44. Tibial sizing plate is then detached from tibia 18 and the provisional tibial prosthesis and offset stem can be installed to test the fit of the components. The tibial prosthesis implant and offset stem implant are then installed.

In the embodiment shown, bushing 16 is received within opening 22 and against recessed shoulder 26 of tibial sizing plate 14. However, it is to be understood that tibial sizing plate 14 may include a different structure associated with opening 22 for receiving bushing 16 and rotatably supporting bushing 16. For example, tibial sizing plate 14 could be configured with an opening including an annular recess at the inner periphery thereof, and bushing 16 may include an annular recess at the exterior periphery thereof. A split ring could be disposed in each of the annular recesses of the bushing and the inner periphery of the opening (not shown), thereby interconnecting the bushing with the tibial sizing plate. Other ways of interconnecting tibial sizing plate 14 with bushing 16 are also contemplated and within the scope of this invention.

Figure 7:
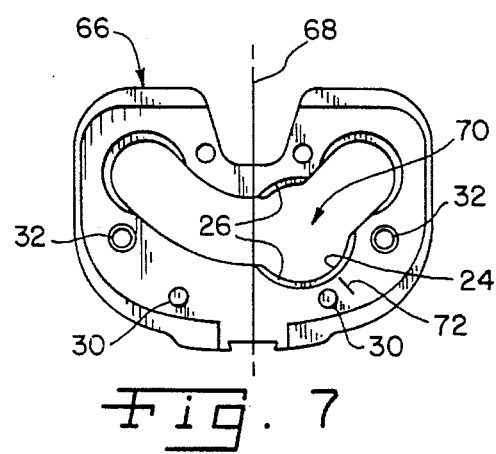
FIG. 7 is a top view of another embodiment of the tibial sizing plate of the present invention.

Referring now to FIG. 7, another embodiment of a tibial sizing plate 66 is shown. With regard to the outer periphery thereof, it can be seen that tibial sizing plate 66 defines an axis of symmetry 68. An opening 70 including a recessed shoulder 26 therein is disposed offset from axis of symmetry 68. Disposed adjacent to opening 70 is an alignment mark 72 for use in conjunction with alignment indicia 42 of bushing 16, described above. Tibial sizing plate 66 is otherwise the same as tibial sizing plate 14, and likewise includes locating pins 30 and holes 32.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic instrumentation assembly located relative to an elongated member, the elongated member adapted for attachment to a bone, said instrumentation assembly comprising:

a plate member having an opening therein defining an inner periphery, and a recessed shoulder disposed about said inner periphery; and a bushing adapted for placement in said opening and against said recessed shoulder, said bushing having a central longitudinal axis, said bushing further having a bore therethrough for receiving the elongated member, said bore disposed substantially parallel to and offset from said longitudinal axis;

whereby movement of one of said bushing and said plate member relative to the elongated member causes a resultant movement of an other of said bushing and said plate member relative to the elongated member such that the bushing is rotated as a result of such movement while the elongated member remains in a stationary position.

2. The orthopaedic instrumentation assembly of claim 1, whereby rotation of said bushing relative to the elongated member causes said plate member to move relative to the elongated member.

3. The orthopaedic instrumentation assembly of claim 1, whereby movement of said plate member relative to the elongated member causes said bushing to rotate relative to the elongated member.

4. The orthopaedic instrumentation assembly of claim 1, wherein the elongated member is adapted for temporary attachment to the bone.

5. The orthopaedic instrumentation assembly of claim 1, wherein said plate member comprises a tibial sizing plate.

6. The orthopaedic instrumentation of claim 1, wherein said bore is disposed offset from said longitudinal axis a distance between about 0.1 to 12 millimeters.

7. The orthopaedic instrumentation of claim 6, wherein said bore is disposed offset from said longitudinal axis a distance of about 4.5 millimeters.

8. The orthopaedic instrumentation assembly of claim 1, wherein said plate member includes a bottom surface for placement against the bone, said recessed shoulder disposed at an angle of between about 0° to 10° relative to said bottom surface.

9. The orthopaedic instrumentation assembly of claim 1, wherein said plate member includes an axis of symmetry, said plate opening disposed along said axis of symmetry.

10. The orthopaedic instrumentation assembly of claim 1, wherein said plate member includes an axis of symmetry, said plate opening disposed offset from said axis of symmetry.

11. An orthopaedic instrumentation assembly located relative to an intramedullary member, the intramedullary member adapted to be disposed at least partially within a bone, said instrumentation assembly comprising:

a bushing having a central longitudinal axis and a bore therethrough for receiving said intramedullary member, said bore disposed substantially parallel to and offset from said longitudinal axis; and a sizing plate having an opening therein, said sizing plate further including means associated with said opening for receiving said bushing, said bushing rotatably supported within said receiving means;

whereby upon movement of one of said bushing and said sizing plate, said bushing and said sizing plate coact to position said sizing plate relative to the intramedullary member such that the bushing is rotated as a result of such movement while the intramedullary member remains in a stationary position.

12. The orthopaedic instrumentation assembly of claim 11, wherein said sizing plate comprises a tibial sizing plate.

13. The orthopaedic instrumentation of claim 11, wherein said bore is disposed offset from said longitudinal axis a distance between about 0.1 to 12 millimeters.

14. The orthopaedic instrumentation of claim 13, wherein said bore is disposed offset from said longitudinal axis a distance of about 4.5 millimeters.

15. The orthopaedic instrumentation assembly of claim 11, wherein said sizing plate includes a bottom surface for placement against the bone, and wherein said receiving means comprises a recessed shoulder disposed within said opening at an angle of between about 0° to 10° relative to said bottom surface.

16. A method of attaching a tibial sizing plate to a proximal end of a tibia, comprising the steps of:

removably attaching an intramedullary member to the tibia;

positioning said tibial sizing plate over said intramedullary member, whereby said intramedullary member extends through an opening in said tibial sizing plate;

sliding a bushing over said intramedullary member, whereby said intramedullary member extends through an offset bore in said bushing;

removably attaching said bushing to said tibial sizing plate, whereby said bushing is at least partially received within said opening;

moving one of said bushing and said tibial sizing plate, whereby said sizing plate moves relative to said intramedullary member; and fastening said tibial sizing plate to the proximal end of the tibia in the desired location.

17. The method of claim 16, wherein said fastening step comprises fastening said tibial sizing plate to the proximal end of the tibia using a plurality of fixation members.

18. The method of claim 16, wherein said intramedullary member comprises an intramedullary reamer, and wherein said moving step comprises moving said tibial sizing plate relative to said intramedullary reamer.

19. The method of claim 16, wherein the method further comprises the steps of:

subsequently removing said intramedullary member and said bushing, leaving an intramedullary canal opening in the tibia having a first axis;

attaching a guide to the tibial sizing plate; and forming a recess through an opening in said guide and through said opening in said tibial sizing plate, said recess having a second axis which is offset from the first axis of the canal.

20. The method of claim 16, wherein the method further comprises the step of sliding a symmetrical bushing having a centrally located bore over said intramedullary member prior to the step of sliding the bushing having the offset bore, to determine if said tibial sizing plate provides appropriate coverage of the proximal end of the tibia utilizing the symmetrical bushing, and wherein if appropriate coverage is not provided, then removing said symmetrical bushing and subsequently proceeding to the step of sliding the bushing having the offset bore over the intramedullary member.

21. A method of attaching a sizing plate to an end of a bone, comprising the steps of:

removably attaching an intramedullary member to the bone;

positioning said sizing plate over said intramedullary member, whereby said intramedullary member extends through an opening in said sizing plate;

sliding a bushing over said intramedullary member, whereby said intramedullary member extends through an offset bore in said bushing;

removably attaching said bushing to said sizing plate, whereby said bushing is at least partially received within said opening;

moving one of said bushing and said sizing plate, whereby said bushing rotates and sizing plate moves relative to said intramedullary member; and fastening said sizing plate to the end of the bone in the desired location.

* * * * *